United States Patent [19]

Hahn et al.

[11] Patent Number: 4,877,017

[45] Date of Patent: Oct. 31, 1989

[54] APPARATUS FOR NON-CONTACTING DISINTEGRATION OF CONCRETIONS

[75] Inventors: Alfred Hahn; Georg Vogel, both of Erlangen, Fed. Rep. of Germany

[73] Assignee: Siemens Aktiengesellschaft, Berlin and Munich, Fed. Rep. of Germany

[21] Appl. No.: 302,144

[22] Filed: Jan. 27, 1989

Related U.S. Application Data

[63] Continuation of Ser. No. 860,590, May 7, 1986, abandoned.

[30] Foreign Application Priority Data

May 28, 1985 [DE] Fed. Rep. of Germany ....... 3519127

[51] Int. Cl.$^4$ ............................................. A61B 17/22
[52] U.S. Cl. .................................. 128/24 A; 128/328
[58] Field of Search ...................... 128/24 A, 328, 660, 128/64

[56] References Cited

U.S. PATENT DOCUMENTS

| 4,539,989 | 9/1985 | Forssmann et al. | 128/328 |
| 4,617,931 | 10/1986 | Dory | 128/328 |
| 4,705,026 | 11/1987 | Chaussy et al. | 128/24 A |

FOREIGN PATENT DOCUMENTS

| 0081639 | 9/1982 | European Pat. Off. |
| 2722252 | 11/1978 | Fed. Rep. of Germany . |
| 2852560 | 1/1980 | Fed. Rep. of Germany . |
| 3122056 | 12/1982 | Fed. Rep. of Germany . |
| 3220751 | 12/1983 | Fed. Rep. of Germany . |
| 3328051 | 2/1985 | Fed. Rep. of Germany . |
| 3336252 | 4/1985 | Fed. Rep. of Germany . |

OTHER PUBLICATIONS

"Extracorporeal Shock Wave Lithotripsy", Chaussy et al. (1982).

Primary Examiner—Michael H. Thaler
Attorney, Agent, or Firm—Hill, Van Santen, Steadman & Simpson

[57] ABSTRACT

The apparatus for non-contacting disintegration of concretions situated in a life form includes a patient bed, a shock wave generator secured on a carriage below the surface of the bed with an arrangement for coupling energy from the shock wave generator positioned between the generator and the bed; an X-ray unit being mounted for pivotable movement on a longitudinal axis and used for positioning the patient with the isocenter of the region to be treated to lie on the longitudinal axis at a space above the surface of the bed and the carriage for the shock wave generator moving the focal point of the shock wave generator along said longitudinal axis from a working position with the energy focused on the isocenter to a remote position. The arrangement for mounting the X-ray unit includes a C-shaped carrier, which will pivot around the longitudinal axis and positions the X-ray radiator or emitter on an opposite side from the radiation receiver. In addition, the apparatus will pivot the shock wave generator around the same longitudinal axis and the C-shaped carrier is preferably pivotable around a second axis perpendicular to the longitudinal axis.

4 Claims, 1 Drawing Sheet

APPARATUS FOR NON-CONTACTING DISINTEGRATION OF CONCRETIONS

This is a continuation of application Ser. No. 860,590, filed May 7, 1986, now abandoned.

BACKGROUND OF THE INVENTION

The present invention is directed to an apparatus for non-contacting disintegrations of a concretion situated in a body of a life form. The apparatus includes a shock wave generator which can have its shock waves focussed or concentrated at an isocenter and the generator is aligned with the isocenter being on the target region in the body. The generator has an arrangement for transferring the energy created by the shock wave generator to the body which arrangement includes a chamber having at least one flexible wall being filled with a coupling agent.

An apparatus with a shock wave generator is employed for example in medicine for disintegrating a renal calculi. Since the apparatus avoids any and all surgical intervention into the body, they are particularly advantageous.

An apparatus having a shock wave generator which concentrates the shock wave on an isocenter and has a container with at least one flexible wall to form means for transferring the shock waves between the generator and a body is disclosed in copending U.S. application, Ser. No. 634,021, filed July 24, 1984 now U.S. Pat. No. 4,674,505 which issued on June 23, 1987 as U.S. Pat. No. 4,674,505 and claims priorty from German OS 33 28 051. The shock wave generator of this copending application is placed with flexible wall lying against the life form. The shock waves are focused onto a focal point such as the isocenter in the target region. It is therefore necessary to position the life form with reference to the shock wave generator so that the concretion which is to be disintegrated will lie precisely in the target region at this focal point or isocenter.

SUMMARY OF THE INVENTION

The present invention is directed to an improvement in an apparatus which easily locates the concretion to be treated and easily centers a shock wave generator after locating the concretion. This shock wave generator is alignable so that the shock waves do not strike sensitive body organs in so far as possible.

To achieve these objects, the present invention is directed to an improvement in an apparatus for non-contacting disintegration of a concretion situated in a body of a life form, said apparatus including a shock wave generator focusing the shock waves at a focal point on an isocenter which is positioned in a target region in the body and includes coupling means for transferring energy from the generator to the body, said coupling means including a chamber with at least one flexible wall being filled with a coupling agent. The improvements comprising a patient bed having a surface extending in a longitudinal direction for receiving a body, a carriage supporting the shock wave generator for pivotal movement around a longitudinal axis spaced above the surface of the bed with the shock wave generator being positioned below the surface of the bed with the coupling means located between the generator and the bed with the focal point being on the longitudinal axis, and carriage being moveable along the longitudinal axis from a working position with its focal point on the isocenter and a second remote position with its focal point moving on said axis, an X-ray unit with an X-ray emitter and radiation receiver and a C-shaped carrier mounting the receiver and emitter on opposite sides of the bed at the working position and C-shaped carrier having a pivot point lying on the longitudinal axis.

With the apparatus of the invention, the locating an alignment of the concretion is possible with the assistance of the X-ray unit while the shock wave generator is withdrawn from the region to be treated. The shock wave generators is subsequently moved into its operating or working position at which the shock wave are focused onto the isocenter.

DESCRIPTION OF THE PREFERRED EMBODIMENTS

Figure 2:
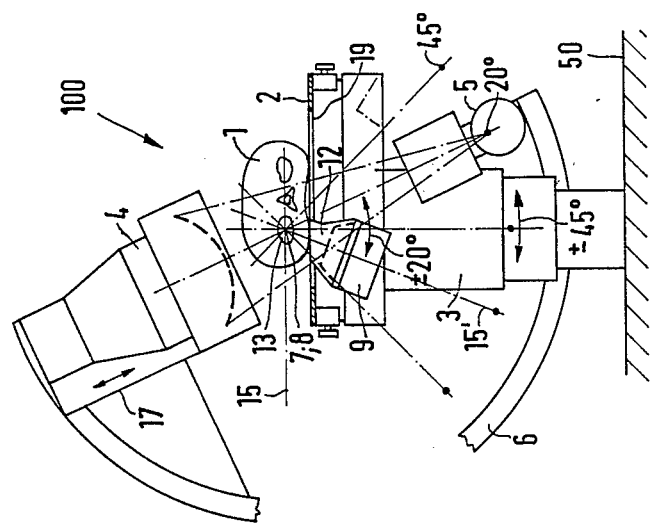
FIG. 2 is an end view with portions broken away for purpose of illustration of the apparatus accordance with the present invention.
Figure 1:
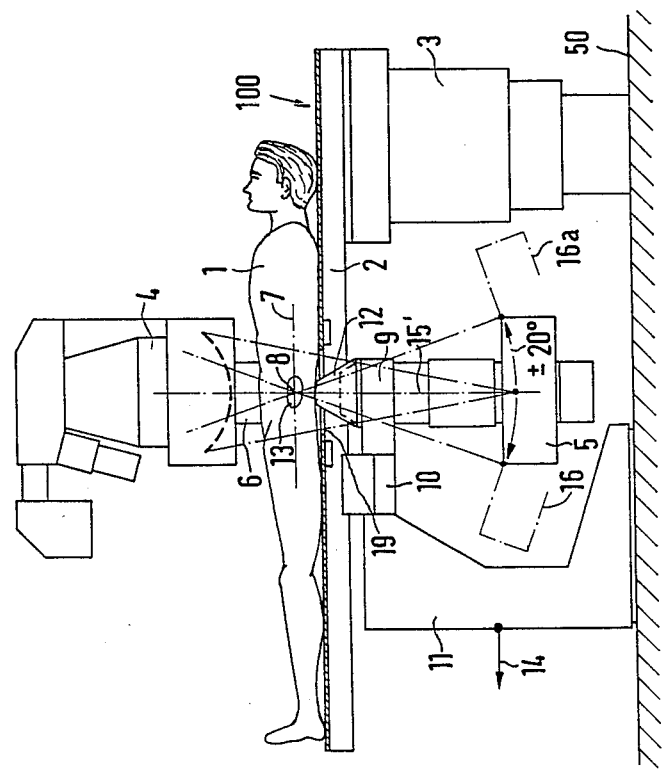
FIG. 1 is a side view of the apparatus in accordance with the present invention.

The principles of the present invention are particularly useful in an apparatus generally indicated at 100 in FIGS. 1 and 2. The apparatus 100 includes a patient bed 2 for receiving a patient 1. The patient bed 2 is secured on a pedestal 3 which can be adjusted to vary the heighth of the bed above a floor surface 50. In addition, the patient bed is also adjustable in a longitudinal and transverse direction relative to the pedestal 3.

An X-ray unit, which comprises an X-ray emitter such as in X-ray radiator 5 and an X-ray receiver such as an X-ray image intensifier 4, is provided for locating and for aligning the patient 1. The components 4 and 5 are secured on a C-shaped carrier 6 to be on opposite sides of the bed 2 as illustrated in the FIGS. 1 and 2. As illustrated, the carrier 6 is pivotable around a horizontal axis 7 which extends parallel to a surface of the bed 2 and spaced thereabove to extend in the longitudinal direction of the bed. As illustrated, the carrier 6 positions the components 4 and 5 at the working position with an isocenter 8 located therebetween.

The support for the carrier 6, which is not shown, can be rotatably situated to rotate around a cross axis or second axis 15 (FIG. 2) so that an oblique in radiation in the direction of the patient is additionally obtainable. This rotation on the axis 15 is illustrated in FIG. 1 as a plus or minus final position 16 and 16a. The cross axis 15 as illustrated extends perpendicular to the axis 7 in a plane which is parallel to the surface of the patient bed 2.

In order to position the image intensifier 4 relative to an isocenter 8 in response to the thickness or size of the patient 1, a guide track 17 is provided in the arrangement for mounting the image intensifier on the carrier 6.

When in the operating or working position, a shock wave generator 9 is aligned to have a focal point at the isocenter 8. The shock wave generator 9 is secured to a C-shaped carrier 10, which in turn is connected to a carriage 11, which can be moved on the floor 50 in the direction of the axis 7. The shock wave generator 9 includes a container 12 having at least one flexible wall on its upper surface. The container 12 is capable of being inflated with a coupling agent, for example with water. For the purpose of coupling the shock wave generator 9 to the patient 1, the bed 2 has a clearance with an aperture 19 in the region of the kidneys of the patient 1. Thus the container 12 can extend into the aperture 19 to engage a surface of the body 1 as illustrated.

For the purpose of disintegrating a concretion, for example a renal calculus 13, the shock wave generator 5 is first moved out of the treatment region in the direcion of arrow 14 with its container or bubble 12 uninflated. The patient is adjusted in a longitudinal and transverse direction and in heighth until the renal calculi 13 lies in the isocenter 8. The alignment of the patient occurs with the assistance of the X-ray image generated by the X-ray image intensifier 4. A transillumination of the patient from various directions is possible by turning the carrier 6 with the X-ray units 4 and 5 around both the axis 7 and around the second axis 15. After alignment of the patient, the carriage 11 is displaced in the direction opposite to that of arrow 14 until the shock wave generator 9 lies in the operating position under the isocenter 8. The bubble or container 12 is subsequently inflated with the coupling agent until it extends through aperture 19 and lies against the surface of the body of the patient 1. The shock wave treatment can then occur.

As is best illustrated of FIG. 2, the shock wave generator 9 is seated on the carrier 10 so that its axis 15' can be pivoted relative to the vertical axis by plus or minus 20°. It is thereby possible to optimumly select a radiation direction so that the body organ, which should not be subject to the shock waves, can be protected therefrom. In addition, the X-ray units 4 and 5 as well as the carrier 6 is adjustable relative to the shock wave generator 9 during treatment by pivoting the carrier 6 so that the shock wave generator 9 will not be imaged in the X-ray picture or at least not disturb it.

The cardonic suspension around the isocenter 8 can also be realized. This additionally allows an oblique irradiation of the longitudinal direction of the patient.

In summary, the following can be stated in regard to the illustrated apparatus:

1. A locating adjustment of the concretion to be treated is possible when the shock wave generator is moved into an operating position.

2. Since the C carrier 6 is pivotable around the axis 7 and also around the second axis 15, which is perpendicular to the first axis 7, the viewing of the concretion can occur along various directions.

3. The X-ray image intensifier 4 can be adapted in size to the respected requirements.

4. X-ray pictures are possible with an X-ray radiator 5 being positioned below or above the bed 2. Given the X-ray radiator or emitter 5 lying above the patient bed, good geometrical pick-up conditions will occur for final exposure in an a.p. direction. With the X-ray radiator emitter 5 lying below the patient bed, good radiation protection will occur.

5. The shock wave generator 9 is continuously pivotable about the axis 7 by plus or minus 20° and allows optimum in radiation of the isocenter 8.

6. The apparatus is universally employable, for example a percutaneous calculus removal is also possible utilizing either a variable or interchangeable patient beds.

Although various minor modifications may be suggested by those versed in the art, it should be understood that we wish to employ within the scope of the patent granted hereon, all such modifications as reasonably and properly come within the scope of our contribution to the art.

We claim:

1. In an apparatus for a non-contacting disintegration of concretion situated in a body of a life form, said apparatus including a shock wave generator having energy waves being focused at a focal point on an isocenter positioned in a target region of the body, said generator having coupling means for transferring the energy from the generator to the body, said coupling means including a container having at least one flexible wall and being filled with a coupling agent, the improvements comprising a patient bed having a surface extending in a longitudinal direction for receiving a body, said bed having an aperture through said surface in an area below said isocenter, a carriage supporting the shock wave generator for pivotal movement around a longitudinal axis spaced above the surface of the bed and extending parallel to the longitudinal direction with the shock wave generator being below the bed with the coupling means located between the generator and bed and the focal point being on said longitudinal axis, said carriage being moveable along the longitudinal direction from a working position with the coupling means extending through the aperture and the flexible wall contacting said body to a removed position with the focal point being moved along the longitudinal axis, an X-ray unit with an X-ray emitter and radiator receiver, and means for separately adjusting the position of the X-ray unit while the shock wave generator is in the working position comprising a C-shaped carrier mounting the receiver and emitter on opposite sides of the bed at the working position and having a pivot point lying on said longitudinal axis so that while the shock wave generator is treating a patient, the X-ray unit can be adjusted and operated without imaging the generator on an X-ray image.

2. In an apparatus according to claim 1, wherein the C-shaped carrier in addition to being pivotable around the longitudinal axis is also pivotable around a second axis extending perpendicular to the longitudinal axis and lying in a plane extending parallel to the surface of the patient bed.

3. In an apparatus according to claim 1, wherein the coupling means has means for changing the amount of coupling agent within the container so that the container is changeable from an inflated condition with the flexible wall extending through the aperture of the bed to engage the surface of the body and an uninflated condition with the flexible wall withdrawn from the aperture to allow the carriage and generator to be moved to the removed position.

4. In an apparatus for a non-contacting disintegration of concretion situated in a body of a life form, said apparatus including a shock wave generator having energy waves being focused at a focal point on an isocenter positioned in a target region of the body, said generator having coupling means for transferring the energy from the generator to the body, said coupling means including a container having at least one flexible wall and being filled with a coupling agent, the improvements comprising a patient bed having a substantially planar surface extending in a longitudinal direction for receiving the body, said planar surface of the bed having an aperture in an area below said isocenter, a carriage supporting the shock wave generator for pivotal movement around a longitudinal axis spaced above the planar surface of the bed and extending parallel to the longitudinal direction with the shock wave generator being below the bed with the coupling means located between the generator and bed and the focal point being on said longitudinal axis, said carriage being movable along the longitudinal direction from a working position with the coupling means extending through the aperture and the flexible wall contacting said body to a removed position with the focal point being shifted along the longitudinal axis, an X-ray unit with an X-ray emitter and radiator receiver, and means for separately adjusting the position of the X-ray unit while the shock wave generator is in the working position, said means for separately adjusting comprising a C-shaped carrier mounting the receiver and emitter on opposite sides of the bed at the working position, said carrier being movable around said longitudinal axis at a pivot point and being movable around a second axis, which extends perpendicular to the longitudinal axis and through the pivot point and which is in a plane extending parallel to the planar surface of the patient bed so that while the shock wave generator is treating a patient, the X-ray unit can be adjusted and operated without imaging the generator on an X-ray image.

* * * * *